United States Patent [19]

Cook et al.

[11] Patent Number: 4,484,141

[45] Date of Patent: Nov. 20, 1984

[54] DEVICE FOR ISOELECTRIC FOCUSING

[75] Inventors: Richard B. Cook, Rockland, Me.; Calvin A. Saravis, Waban, Mass.; Peter Lefferson, St. Petersburg, Fla.

[73] Assignee: FMC Corporation, Philadelphia, Pa.

[21] Appl. No.: 441,018

[22] Filed: Nov. 12, 1982

[51] Int. Cl.³ .............................................. G01N 27/62
[52] U.S. Cl. .................................... 324/464; 324/71.1
[58] Field of Search ...................... 324/71.1, 71.4, 464, 324/140 R; 204/180 R, 180 G, 299 R

[56] References Cited

U.S. PATENT DOCUMENTS

| | | | |
|---|---|---|---|
| 3,664,939 | 5/1972 | Luner et al. | 204/299 R |
| 3,772,593 | 11/1973 | Sidhu | 324/71.1 |
| 4,375,401 | 3/1983 | Catsimpoolas | 204/299 R |
| 4,433,299 | 2/1984 | Kawai et al. | 324/464 |
| 4,443,319 | 4/1984 | Chait et al. | 204/299 R |

Primary Examiner—Michael J. Tokar
Assistant Examiner—Kevin D. O'Shea

Attorney, Agent, or Firm—Robert D. Jackson; Eugene G. Seems

[57] ABSTRACT

A device for detecting the isoelectric end point in an isoelectric focusing system by electronically integrating, over successive time intervals, a characteristic of the electrical input to said zone as it varies with the increasing resistance of the zone. Most conveniently, the measured characteristic is the current through the zone which, under constant impressed voltage or power, asymptotically approaches a minimum value as the end point is reached.

The measured characteristic is continually converted to a sequence of pulses indicative of the value of the characteristic. The end point is indicated when the difference between counts of these pulses over successive time intervals reaches a preselected value. At the end point, provision is made for replacement of the focusing voltage with a lower voltage to keep the ampholytes focused. A signal can be activated at the end point.

5 Claims, 1 Drawing Figure

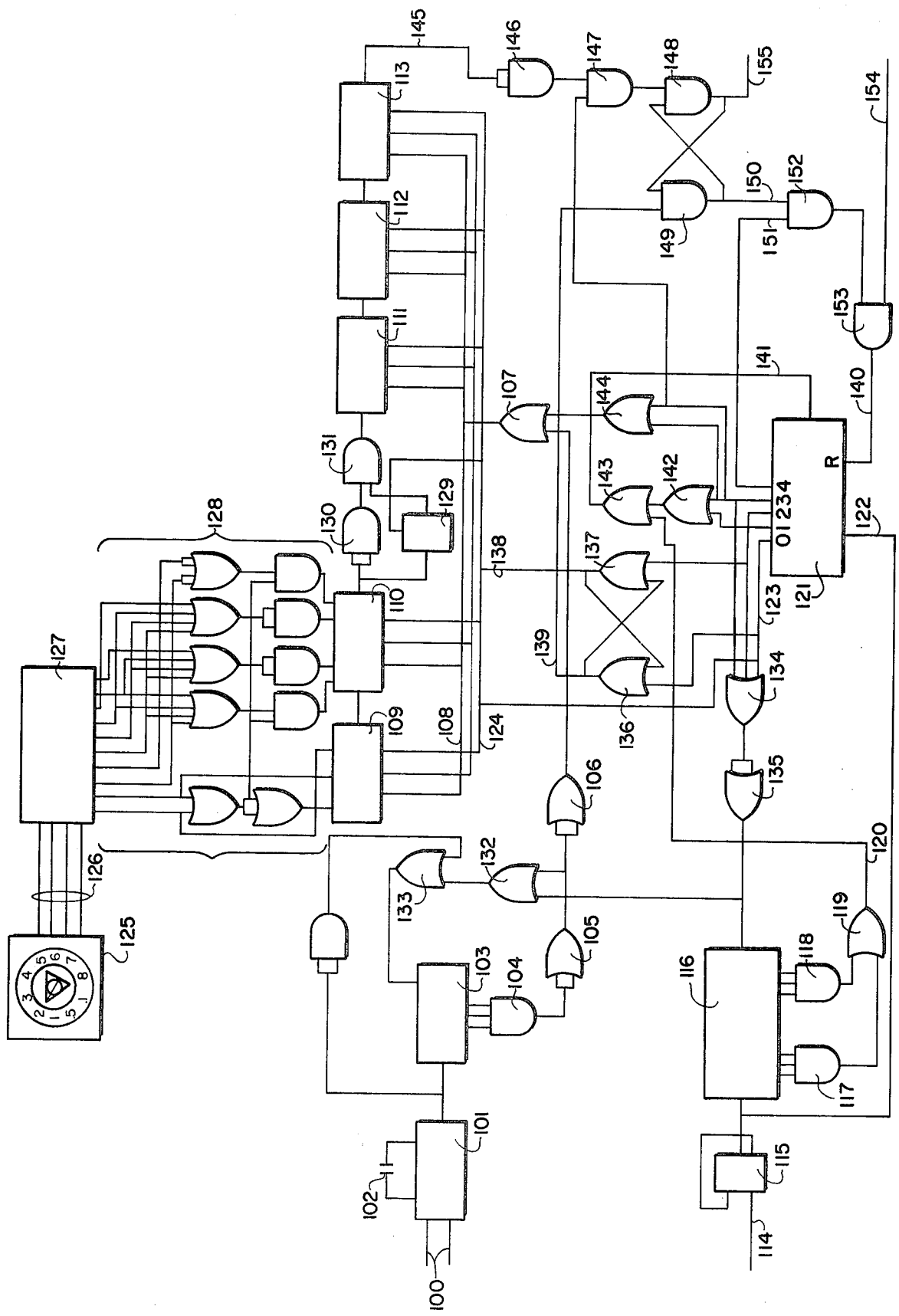

DEVICE FOR ISOELECTRIC FOCUSING

This invention relates to electrophoretic processes. In particular, the invention pertains to isoelectric focusing and a device for use therewith.

Isoelectric focusing (IEF) is a well-known electrophoretic technique for separating and characterizing amphoteric macromolecules, such as proteins and the like, by causing them to segregate at their isoelectric points along a stable pH gradient. The method is used on both an analytical and preparative scale.

Briefly, IEF can be described as follows:

A stable pH gradient is formed by the electrophoresis of carrier ampholytes in a suitable medium, for example, an anticonvective medium, such as agarose gel. The pH gradient increases progressively from anode to cathode. When introduced into this system, a mixture of proteins or other amphoteric molecules will, depending on their individual surface charge, commence moving under the influence of the electric field. In the event the initial charge of a given member is positive, it will migrate towards the cathode into regions of higher pH. As it continues to move through the pH gradient, the molecule gradually loses positive charges while acquiring negative charges. This can occur, for example, through deprotonation of carboxyl or amino groups in a protein. Eventually, the migrating entity reaches a point in the pH gradient where its net electrical charge is zero, that is, its isoelectric pH (pI), and is said to be focused. This is the isoelectric end point. Diffusion of focused molecules away from their pI will cause them to once again become charged whereby they will electrophoretically migrate back to their pI. By thus neutralizing diffusion with an electrical field of sufficient strength, an ampholyte macromolecule will come to an equilibrium position where it may be concentrated into an extremely sharp band. Of course, the degree of resolution of an ampholyte mixture is a function of the slope of the pH gradient; the shallower the gradient between any two pH points, the better the separation.

After focusing is complete, the segregated sample components in the case of preparative IEF are physically recovered from the focusing medium. In analytical IEF, the pH gradient is commonly established in a thin layer of gel which is coated on a glass or plastic support. A sample to be identified is placed on the gel layer and the plate connected to a source of direct current. Under the influence of the electric field, the sample components focus as sharp bands corresponding to their pI. Several samples can be run simultaneously in adjacent channels of the gel plate. The plate is then treated to remove carrier ampholytes, washed, stained to increase the visibility of the bands and then dried to provide a permanent record of the analysis.

Basically, an IEF system consists of an IEF zone and a source of direct current of the requisite voltage for providing the electric field across the IEF zone. This system constitutes a closed electrical circuit that can be analyzed in accordance with Ohm's Law. At the beginning of a typical IEF run with the power supply set at, for instance, either constant voltage or a constant power output, the resistance of the medium is lowest due to the abundance of highly conductive ampholyte ions. As the run continues, however, the loss in net charge by the migrating ions causes a reduction in their current carrying capacity with concomitant increase in the resistance of the medium. At the same time, there is a proportionate decrease in the current. Initially, such decrease in the current proceeds at a high rate, but as the ions approach their pI in the gradient, the rate of decrease rapidly slows and the slope of the current becomes asymptotic. As a consequence, it is difficult to gauge when focusing is complete owing to the low rate of current change at this stage of the process—even after a substantial time interval. If the run is terminated prematurely, focusing will be incomplete and maximum resolution will not be attained. On the other hand, if the run is allowed to continue after focusing is complete, commonly referred to as overfocusing, the ampholytes and even the gel medium can suffer damage from resistive (joule) heating.

Relatively few methods for determining the IEF end point have been proposed.

One method entails measuring the time required to achieve pH gradient linearity. Once pH gradient linearity is reached, it is assumed that all sample materials will have oriented themselves in the pH gradient as a function of the respective isoelectric point (pI). This method suffers from two disadvantages. The first is that the IEF run must be interrupted in order to measure the pH in different regions of the IEF medium and thereby determine the pH gradient. Early applications of this method were very tedious and destructive of the IEF gel medium in that they required removal of small gel plugs from a series of measured positions in the gradient. The pH of these gel plugs was then determined after maceration in distilled water and the pH values plotted as a function of the length of the gradient.

More recently, surface pH electrodes have been developed which permit measurement of the surface pH at any point in the gradient. This technique still results in some physical damage to the gel due to the fact that the electrode must be firmly pressed onto the gel surface in order to obtain reliable readings. Since IEF gels are typically constructed from rather fragile gel media, this results in some gel destruction. This method is further complicated by the fact that the electrical power must be shut off for safety reasons before the pH gradient can be determined. Turning the power off, however, results in diffusion of the pH gradient. In other words, the pH gradient will be changing while it is being measured. Perhaps the greatest drawback to this method of assigning an IEF end point is that all sample components will not focus in the pH gradient as rapidly as the relatively low molecular weight carrier ampholytes. On the contrary, sample components will approach their pI as a function of both their total charge and as a function of the sieving characteristics of the IEF medium. Using the pH gradient linearity method, then, it would be quite possible to determine two different pIs for the same protein in two different IEF gels having different sieving characteristics. It is also not convenient to allow the focusing to proceed substantially beyond the point where the pH gradient is linear because numerous phenomena begin to occur which render the gradient non-linear and thereby confound unequivocal pI determination. These phenomena include complexation of ampholytes and decomposition of the IEF media.

A second method for determining IEF end point entails application of the sample mixture at opposite ends of the same pH gradient. This is done in two adjacent "lanes" of the same pH gradient so that a determination of when the sample component bands are in alignment can be made. In order to visualize most samples, however, it is necessary to stop the IEF run and develop the gel in protein fixative and stain. This might result in numerous gels being run before a suitable time interval to achieve alignment could be determined. The use of colored or visible marker proteins has been developed to somewhat alleviate this difficulty by permitting the visual tracking of the band alignment during the course of the run.

Unfortunately, there are several other problems associated with this method. The first is that many substances will precipitate if applied at certain points in the pH gradient but not in others. For example, proteins are typically least soluble at their pI and therefore would tend to precipitate if applied at a point in the pH gradient corresponding to their pI. Although one might try to avoid that for known materials, this is singularly difficult or impossible for unknowns or even heterogeneous mixtures of known substances having different pIs. A further complication is the fact that various gel phenomena can result in non-alignment of bands in certain regions of the gel. Such phenomena include both electroendosmosis and pH gradient decay due to a variety of causes. As a result, some sample components in a mixture may align in certain regions of the gel but not in others when practicing this dual application approach to end point determination.

Various instruments have been used to aid in the termination of an IEF run. The simplest of these is a timer. Using this technique, the operator would determine the length of time required to reach an empirical end point under a given set of conditions. When those conditions were repeated, he could set the time for the same length of time and hope to obtain equivalent results. Although timers have been built into commercial electrophoresis power supplies or accessory apparatus, they merely sound an alarm and either continue with the preset voltage or shut it off completely. However, permitting the run to continue may cause distortion in the gradient and stopping the run completely may allow the bands to diffuse. Recently, a more sophisticated timer has been introduced which integrates the voltage applied over the time course of the run. This timer has been called a volt-hour integrator and can be used either to count the total number of volt hours applied or to signal when a preset number of volt hours has been reached. In the latter mode of operation, no automatic interruption or alteration of power occurs when the preset time interval has elapsed. To that extent, both of these methods require that the operator be present and prepared to shut the unit off as soon as the timers go off. Although this procedure is inconvenient on a routine basis, it is nevertheless very important due to the many artifacts and other problems which can result from overfocusing an IEF gel.

From the foregoing, it can be seen that there is a need of further improvements for determining the end point in an IEF system. The development of such improvements, however, has proved difficult to realize in practice.

In accordance with the present invention, there is provided a device for detecting the isoelectric end point in an isoelectric focusing zone, said device comprising:

(a) means for integrating a said characteristic of electrical input over two successive periods of time each of sufficient duration to provide a statistically representative indication of the change of said characteristic between the two periods, (b) means for comparing the values of the integrals so obtained for said successive time periods, (c) means for setting said device to detect a particular differential between said values which is indicative of the reaching of the isoelectric end point, (d) means for causing the recurrence of the operation of means (a) and means (b) whenever the differential between the values compared by means (b) fails to reach the value set by means (c), and (e) means for effecting an alerting or terminating function when the differential between values compared by means (b) reaches or passes the value set by (c).

In carrying out the invention, the isoelectric end point is preferably determined by a technique in which the current passing through the isoelectric focusing device is monitored by a pulse generator which produces a sequence of pulses having a pulse frequency which varies with the magnitude of the current, the number of pulses generated in each of two successive equal time periods is counted and compared and, when the difference between these two pulse counts is equal to or less than the number preselected as indicating for practical purposes the isoelectric end point, the focusing voltage is removed from across the isoelectric focusing device and is replaced by a lower holding voltage which retards diffusion of the focused ampholytes.

One embodiment of a device for determination of isoelectric end point in this manner is illustrated in the accompanying drawing, which shows a schematic diagram of a logic circuit for accomplishing this result, the ground and power connections being omitted for the sake of clarity.

Information as to the current passing through the isoelectric device is fed to the device shown in the drawing by means of leads 100 which may be connected across a resistor (not shown) through which passes the current being measured so that the voltage across the leads is proportional to the current. These leads feed into the voltage-to-frequency converter 101 which can for instance be a type of AD537 integrated circuit. The input parameters can conveniently be chosen so that for current values varying between 0.1 milliampere and 100 milliamperes the voltage across lead 100 varies from 2.5 millivolts to 2.5 volts. Suitable filter means (not shown) can be provided before input 100 to minimize transitory fluctuations in the input signal. The output of the converter 101 can conveniently be arranged, by provision of a capacitor 102, as is known in the art, to yield a frequency range of 100 hertz to 100 kilohertz over this input voltage range. In this frequency range, an essentially linear response is obtained.

By means of binary counter 103 with its third, sixth and seventh stages providing the input into NAND gate 104, the frequency output of converter 101 is divided by 100, thus resulting in a frequency output from the NAND gate varying between 1 hertz and 1000 hertz. It is the pulses in this frequency range which are fed through NOR gates 105, 106, and 107 into the counter by means of lead 108. Binary counter 103 may be a type 4040 integrated circuit with the output from NOR gate 105 fed to its reset terminal through NOR gates 132 and 133 to provide recurring pulses.

The main counter system is shown as composed of five cascaded decade counters 109, 110, 111, 112 and 113, which can conveniently be type 4510 integrated circuits, permitting counting up to 100,000 pulses. With such a counter system and with the pulse frequencies referred to above, the time period over which pulses are counted as an indication of the state of the current through the isoelectric focusing device can conveniently be selected as one minute since in a one minute interval an input frequency of 100 kilohertz, corresponding to a current of 100 milliamperes, will deliver 60,000 pulses.

With such an arrangement, changes in current through the isoelectric focusing apparatus as small as 0.1 milliampere per hour can be detected, such a change in current producing a difference of one pulse between successive one minute pulse counts. Typically, current changes of between 0.1 milliampere per hour and 10 milliamperes per hour, corresponding to pulse count differences of between one and 100, can be selected as indicative of the practical isoelectric end point in the usual procedures.

The device shown in the drawing incorporates a timing arrangement which provides a timing pulse at one minute intervals to control the timing of the pulse count. A clock device (not shown) provides a 500 hertz input at lead 114 as input to flip-flop 115 which can, for instance, be one half of a 4013 type cross-coupled integrated circuit. The flip-flop, operating as a binary divider, produces an output of 250 hertz. By means of 14 stage binary counter 116, which can be a 4020 type integrated circuit, connected at its fourth, fifth, eighth and tenth stages with the inputs of a first NAND gate 117 and at its twelfth, thirteenth and fourteenth stages with a second NAND gate 118, the outputs of which are connected to the inputs of NOR gate 119, a single pulse is provided on lead 120 each minute.

The sequencing of the operating steps in the determination of the isoelectric end point is controlled by decade counter 121, which can be a 4017 type integrated circuit and which is used as a stepping switch. The switch is stepped from stage to stage by the 250 hertz signal from flip-flop 115 which is introduced into the clock input of the switch by lead 122.

Initially the zero stage output of switch 121 is high, all other outputs being low. Lead 123 from this stage connects with lead 124 which in turn is connected to the preset enable terminals of counters 109, 110. With the preset enable high, a pulse count corresponding to the state of the binary load terminals of the counters 109, 110 is loaded into these counters. In this manner the counters are preset with a pulse count representing the rate of current change through the isoelectric focusing device selected as representing the isoelectric end point. In the arrangement shown, 99 pulses will correspond to 0.1 milliampere per hour and 20 pulses will represent 8 milliamperes per hour.

A binary coded decimal switch is provided which has a ten position dial, to any one of which the switch can be set to represent one chosen value of rate of current change. The ten positions shown in the drawing are, respectively, 0.1, 0.5, 1, 2, 3, 4, 5, 6, 7 and 8 milliamperes per hour. These positions are binary encoded by the switch to represent the decimal numbers 1 to 10 and transmitted by lead 126 to binary coded decimal to decimal decoder 127.

The ten outputs of decoder 127 are binary encoded by means of logic arrangement 128 so as to introduce into the binary load terminals of counters 109, 110 a pulse count corresponding to the dial setting of switch 125 upon activation of the preset enable function of these counters.

By means of this preset it is possible for the counter system to indicate the point at which the count of the pulses generated over one minute in accordance with the isoelectric focusing current differs from the pulse count over the preceding minute by not more than the preset number. This is done by presetting the counter effectively in the negative direction by the chosen preset differential, by then counting up through zero and beyond for one minute and then counting down for the next minute. Upon completion of the count up, the number in the counter will represent the isoelectric focusing current count less the chosen preset count. Thereafter, upon the count down, if the current has not decreased by an amount corresponding to the preset count, the counter will not carry out and the counting operation will continue for another minute's count up followed by another minute's count down. When the point is reached at which the current during the second minute count down does not differ from the current during the first minute count up by more than the preset amount, the counter will carry out and actuate the end point operations.

The negative loading of the preset pulse count can be accomplished by loading into counters 109, 110 a number equal to 100 minus the pulse count corresponding to the chosen dial setting and by providing an arrangement whereby the first carry out from counter 110 is not carried into counter 111. Thus, on the up count the counters 109 and 110 must count out a number of pulses corresponding to the dial presetting before beginning the final up count which is cascaded through the complete counter series 109, 110, 111, 112 and 113.

The arrangement which interrupts the carry out from counter 110 on the preset up count but not on the final up count, is provided by flip-flop 129 together with NAND gates 130 and 131.

While stepping switch 121 is in its initial state with the zero stage high, the connection through NOR gates 134, 135, 132 and 133 maintain the reset terminals of binary counters 116 and 103 positive, cutting off pulses from these devices. Flip-flop made up of cross-connected NOR gates 136, 137 is set in the state in which output to lead 138 is high and output to lead 139 is low. Lead 138 is connected to updown terminals of counters 109 to 113 and in this state, the counters are set to count up.

With the system in this condition, lead 140 supplying reset terminal and lead 141 supplying clock enable terminal of stepping switch 121 are at ground, permitting the switch to step to the first stage. At this stage, the reset terminals of binary counters 103 and 116 are returned to ground, allowing generation of pulses by these devices. NOR gate 142 goes low, allowing NOR gate 143 to remain high during the one minute intervals between timing pulses originating with binary counter 116. Lead 141 then maintains the clock enable terminal positive during this one minute interval, inhibiting further stepping of the switch for one minute. NOR gate 144 also goes low, permitting the measuring pulses from binary counter 103 to activate NOR gate 107 and introduce a like number of pulses into the counter system 109 to 113 through lead 108. The counter system counts up until the full count representing the isoelectric focusing current less the preset count is registered as described above.

After one minute, the next timing pulse returns the clock enable of switch 121 to ground, allowing switch 121 to continue stepping. At the second stage, timing and measuring pulses are again interrupted, and flip-flop 136, 137 is reversed so that lead 138 now sets counter system 109 to 113 in the count down state.

As the switch 121 steps to the third stage, the clock enable is again set to interrupt further stepping for one minute and NOR gate 107 is again set to transmit measuring pulses to the counter system 109 to 113, this time causing the system to count down. At the end of one minute, the timing pulse again returns the clock enable of switch 121 to ground and allows the switch to step to the fourth stage.

If during the third stage the counting system 109 to 113 has not counted down to zero, indicating that the isoelectric end point has not been reached, then stepping to the fourth stage will cause switch 121 to be reset to zero and the counting cycle will be repeated.

This resetting will occur since, in the absence of a pulse at the carry out of counter 113, the lead 145 provides a continuously high input to NAND gate 146 so that the output of NAND gate 146 provides a low input to NAND gate 147 and consequently a high input to NAND gate 148 which is cross-connected as a flip-flop with NAND gate 149, the input of which is maintained high by lead 139.

With the flip-flop in this state, lead 150 is high. When lead 151 is also made high by stepping of switch 121 to the fourth stage, the output of NAND gate 152 is caused to go low and the output of NAND gate 153 is caused to go high, thus activating the reset switch 121 by means of lead 140.

Prior to the fourth stage, the reset of switch 121 is held low since both inputs to NAND gate 153 are held high, the lead 154 being connected to an external power source. Lead 154 can be interrupted when an external reset is desired.

If, however, the counting system has counted down to zero while the switch 121 is still set at the third stage, indicating the reaching of the isoelectric end point, pulsing of the carry out of counter 113 will cause the input to NAND gate 148 to go from high to low, resulting in a high output from NAND gate 148 and a low output from NAND gate 149.

Lead 155, which serves as the input to the end point functions (not shown) has hitherto remained low but is now high. When lead 155 goes high it can be arranged to activate or perform various functions attendant the reaching of the isoelectric end point, for example, setting into operation the equipment for replacing the isolectric focusing voltage with the hold voltage and activating whatever sonic or visual warning is desired to alert the operator that the end point has been reached.

It might be assumed that measuring the rate of change in current over successive time intervals in accordance with the invention herein would be relatively straightforward, since the current decrease during IEF is typically shown as a smooth hyperbolic function. In fact, however, it has been found that the rate of change in IEF amperage, rather than being smooth, has an undulating configuration and may vary as much as 100 to 200% over intervals of short duration. So far as is known, such fluctuations of an IEF current have not previously been reported. It is speculated that they are attributable to momentary variations in the resistance of the medium as well as electronic parameter changes by the power supply. The power supply adjusts to maintain the product of voltage and amperage constant (constant power). There is a time delay necessarily involved in effecting this change as the unit must first measure the amperage before adjusting the voltage. Such control loops are believed to contribute to such fluctuations in amperage decay in a medium which is probably undergoing sudden changes in resistance.

Despite the extreme local variations in current rate of change during successive short time intervals, the device of the invention can be programmed so as to reject these fluctuations, thereby precluding the signaling of a premature or false end point. To illustrate this feature, let it be assumed that 8 mA/hr. is selected as the end point slope. Fifteen minutes into the run, but long before the end point (that is, 30 min.) the milliamps in the first minute average 12 by being made up of 10 second average currents of 12, 14, 10, 13, 11 and 12 in that order, and in the second minute average 10 milliamps by being made up of average currents in 10 second intervals of 11, 9, 12, 8, 11 and 9 in that order. Since the counter loads in a tens complement of 8 into the second counter (that is, 20) for the rate of 8 milliamps per hour, the count goes up through zero in the first minute to a total positive count (TPC) where:

TPC = average first minute milliamperage × 600
CTS/ma − 80

If the counts accumulated in the second minute (CAS) equal the TPC, then the counter will go through zero and the detector will signal that an end point has been reached. In the example given, however, it is noted that the detector would not signal an end point, since CAS is less than TPC:

TPC = 12 × 600 − 80 = 7120 counts
CAS = 10 × 600 = 6000 counts

Even though momentary fluctuations of the current were seen due to changing conditions of the gel and automatic compensation by the power supply, the end point would not be falsely tripped.

If at the end of a typical 30 minute run, the current in the first minute averages 10, then TPC will equal 5920. If the current in the second minute averages 9.9 milliamps, then CAS will equal 5940 and the counter will go through zero and trip the circuit to adjust the unit into maintenance voltage and audibly and/or visually signal the operator.

The maintenance voltage is preferably adjustable, typically from about 300 volts to about 500 volts.

The capability of distinguishing current fluctuations from the rate of change of the primary IEF current to avoid signaling premature end points is an important and valuable feature of the herein device. In general, the time intervals for measuring the IEF current so as to reject these current fluctuations are in the interval range of 0.5 minutes to 2.5 minutes, with 1.0 minute intervals being selected in the preferred practice of the invention.

The invention has been described in terms of measurement of current over successive time periods as indicative of the change of electrical resistance in the isoelectric focusing zone associated with the isoelectric end point. It is apparent that measurements of other characteristics of the electrical input to the zone which are indicative of the change in resistance associated with the end point can, in similar manner, be converted to pulse sequences which are counted over successive time periods with the end point being detected when the count difference between successive time periods corresponds to that set to be indicative of the end point.

State of the art commercial power supplies have the capability of presetting maximum or minimum values of voltage, current or power. The power supply, for instance, can be set to maintain the current through the zone no lower than a minimum value higher than the asymptotic value which the current would have at the end point if supplied under constant voltage or power. When the current is at this minimum value, the power supply will operate at constant current and the voltage across the zone will increase at an increasing rate as the end point is reached. The rate change of change in voltage, measured as a differential of pulse counts in successive time periods, can then be used as an indication of the reaching of the end point when compared to a preset differential, that is, the voltage becomes asymptotic.

Similarly, with the power supply set to limit voltage to a preset maximum, the isoelectric focusing can be carried out, for instance at constant power input, until this maximum voltage is reached. Thereafter the system will operate at power input decreasing with time. The rate of change of power input, measured as a differential of pulse counts in successive time periods can then be used as an indication of the reaching of the end point when compared to a preset differential, that is, the power becomes asymptotic

What is claimed is:

1. A device for detecting the isoelectric end point in an isoelectric focusing zone, across which a voltage gradient is established, the electrical resistance of said zone increasing with time under the influence of said gradient, said device comprising:
   (a) means for integrating a characteristic of electrical input over two successive periods of time each of sufficient duration to provide a statistically representative indication of the change of said characteristic between the two periods,
   (b) means for comparing the values of the integrals so obtained for said successive time periods,
   (c) means for setting said device to detect a particular differential between said values which is indicative of the reaching of the isoelectric end point,
   (d) means for causing the recurrence of the operation of means (a) and means (b) whenever the differential between the values compared by means (b) fails to reach the value set by means (c), and
   (e) means for effecting an alerting function when the differential between values compared by means (b) reaches or passes the value set by (c).

2. A device according to claim 1 wherein the measured characteristic of the electrical input to said zone is the current flowing through said zone.

3. A device for detecting the isoelectric end point in an isoelectric focusing zone, across which is established a voltage gradient, the electrical resistance of said zone increasing with time under the influence of said gradient, said device comprising:
   (a) means for generating a sequence of pulses, the frequency of occurrence of which varies in accordance with the resistance of said zone as measured by a characteristic of the electrical input to said zone,
   (b) means for counting the number of said pulses generated in successive time periods and for comparing the number so counted in each of two successive time periods,
   (c) means for setting said device to detect a particular differential between the numbers compared by (b) which is indicative of the reaching of the isoelectric end point,
   (d) means for causing the recurrence of the counting of (b) whenever the differential between the numbers compared by (b) exceeds the value set by (c) and
   (e) means for effecting an alerting function when the differential between numbers compared by (b) becomes equal to or less than the value set by (c).

4. A device according to claim 3 wherein the function to be effected on (e) is a signal which can be perceived by the operator.

5. A device according to claim 3 wherein the function to be effected in (e) is replacing the focusing voltage with a lower voltage capable of maintaining the isoelectric end point.

* * * * *